United States Patent
Lee et al.

(10) Patent No.: US 9,707,222 B2
(45) Date of Patent: Jul. 18, 2017

(54) ISOQUINOLINE ALKALOID DERIVATIVE FOR ACTIVATING AMP-DEPENDENT PROTEIN KINASE

(71) Applicant: ZIH YUAN TANG Biotechnology Co., Ltd, Taipei (TW)

(72) Inventors: Shoei-Sheng Lee, Taipei (TW); Ming-Jai Su, Taipei (TW); Chi-Huan Yeh, Miaoli County (TW); Sheng-Fa Tsai, Taipei (TW); Cheng-Yen Tsai, Taichung (TW); Chi-Tun Ruan, New Taipei (TW); Chao-Min Hsu, New Taipei (TW)

(73) Assignee: ZIH YUAN TANG BIOTECHNOLOGY CO., LTD., Taipei (TW)

( * ) Notice: Subject to any disclaimer, the term of this patent is extended or adjusted under 35 U.S.C. 154(b) by 206 days.

(21) Appl. No.: 14/492,547

(22) Filed: Sep. 22, 2014

(65) Prior Publication Data

US 2015/0335634 A1  Nov. 26, 2015

(30) Foreign Application Priority Data

May 23, 2014 (TW) .............................. 103118128 A

(51) Int. Cl.
*A61K 31/472* (2006.01)

(52) U.S. Cl.
CPC .................... *A61K 31/472* (2013.01)

(58) Field of Classification Search
None
See application file for complete search history.

(56) References Cited

U.S. PATENT DOCUMENTS 7,119,103 B2 * 10/2006 Feller ................... C07D 217/18
514/307

OTHER PUBLICATIONS

"The Influence of Salsolinol on Basic Rat Metabolism" by Kurnik et al., Folia Medica Craco. 12, May 20, 2012.*
Praman et al., J. Ethnopharmacol. 140, 166-78 (2012).*
Dias et al., Planta Med. 70, 328-33 (2004).*

* cited by examiner

*Primary Examiner* — Theodore R West
(74) *Attorney, Agent, or Firm* — WPAT, P.C., Intellectual Property Attorneys; Anthony King

(57) ABSTRACT

The present invention provides a method for activating the AMP-dependent protein kinase (AMPK) in a subject comprising administering the subject with a pharmaceutical composition comprising a pharmaceutically acceptable carrier and a therapeutically effective amount of a compound having the general Formula I, preferably salsolinol or reticuline. The pharmaceutical composition is able to activate AMPK, and thus is effective in the regulation of cell growth and metabolism, and the treatment of AMPK associated diseases.

2 Claims, 4 Drawing Sheets

ISOQUINOLINE ALKALOID DERIVATIVE FOR ACTIVATING AMP-DEPENDENT PROTEIN KINASE

FIELD OF THE INVENTION

The present invention provides a method for activating AMP-dependent protein kinase (AMPK) using an isoquinoline alkaloid derivative.

BACKGROUND OF THE INVENTION

Isoquinoline alkaloid derivatives are a group of nitrogen-containing organic compounds existing in plants and animals in nature. Most of them have a complex ring structure with their nitrogen atom incorporated in the ring. Such isoquinoline alkaloid derivatives, including salsolinol and reticuline, possess significant biological activities. Salsolinol is known to be used mainly for regulation of blood pressure, while reticuline is used mainly as an active ingredient for treating malaria, and also as a component in pain relievers.

AMP-dependent protein kinase (AMPK) is a metabolic or energy sensor of the cells, characterized in that it can bind with AMP and maintain the balance between the generation and consumption of ATP through AMP, and thus maintain the balance of energy metabolism. Meanwhile, AMPK can also modulate cell growth and proliferation, establish and stabilize cell polarity, regulate animal lifespan, and modulate physiological rhythms. In recent years, targeting AMPK activation has become one of the key points in pharmaceutical development. Therefore, the pharmaceutical industry is actively pursuing the development of new AMPK activators.

BRIEF SUMMARY OF THE INVENTION

It is unexpectedly found in the present invention that certain isoquinoline alkaloid derivatives, such as salsolinol and reticuline, are effective in the activation of AMPK.

In one aspect, the present invention provides a method for activating the AMP-dependent protein kinase (AMPK) in a subject comprising administering the subject with a pharmaceutical composition comprising a pharmaceutically acceptable carrier and a therapeutically effective amount of a compound having the general Formula I:

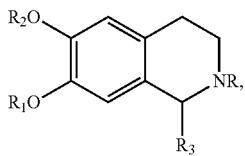

Formula I wherein R, $R_1$ and $R_2$ are each independently H, alkyl or acyl ($R_aCO$) group; $R_3$ is alkyl or substituted benzyl group; wherein $R_a$ is H or alkyl group.

In one embodiment of the present invention, said substituted benzyl group has the following formula II:

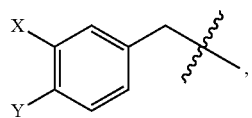

Formula II wherein X and Y are each independently H, OH, methoxy (OMe) or acyloxy ($R_bCO$—O—) group; wherein $R_b$ is H or alkyl group.

In one example of the present invention, said compound having Formula I is salsolinol.

In another example of the present invention, said compound having Formula I is reticuline.

In another aspect, the present invention provides a method for reducing blood glucose in a subject comprising administering the subject with a pharmaceutical composition comprising a pharmaceutically acceptable carrier and a therapeutically effective amount of a compound having the general Formula I of the present invention.

In still another aspect, the present invention provides a method for treating an AMPK-dependent disease in a subject comprising administering the subject with a pharmaceutical composition comprising a pharmaceutically acceptable carrier and a therapeutically effective amount of a compound having the general Formula I of the present invention, wherein the treatment is achieved through the activation of AMPK by the compound having the general Formula I; wherein said AMPK-dependent disease is selected from the group consisting of cancer, cardiovascular diseases, and metabolism diseases. The compound having Formula I of the present invention also has an effect in anti-inflammation or promoting wound healing.

Those and other aspects of the present invention may be further clarified by the following descriptions and drawings of preferred embodiments. Although there may be changes or modifications therein, they would not betray the spirit and scope of the novel ideas disclosed in the present invention.

BRIEF DESCRIPTION OF THE DRAWINGS

The drawings presenting the preferred embodiments of the present invention are aimed at explaining the present invention. It should be understood that the present invention is not limited to the preferred embodiments shown. The data in the figures and examples are shown as mean±standard deviation (SD), determined by the paired t-test. Significant differences are shown as follows: *: P<0.05; **: P<0.01; #: P=0.067.

DETAILED DESCRIPTION OF THE INVENTION

Figure 1:
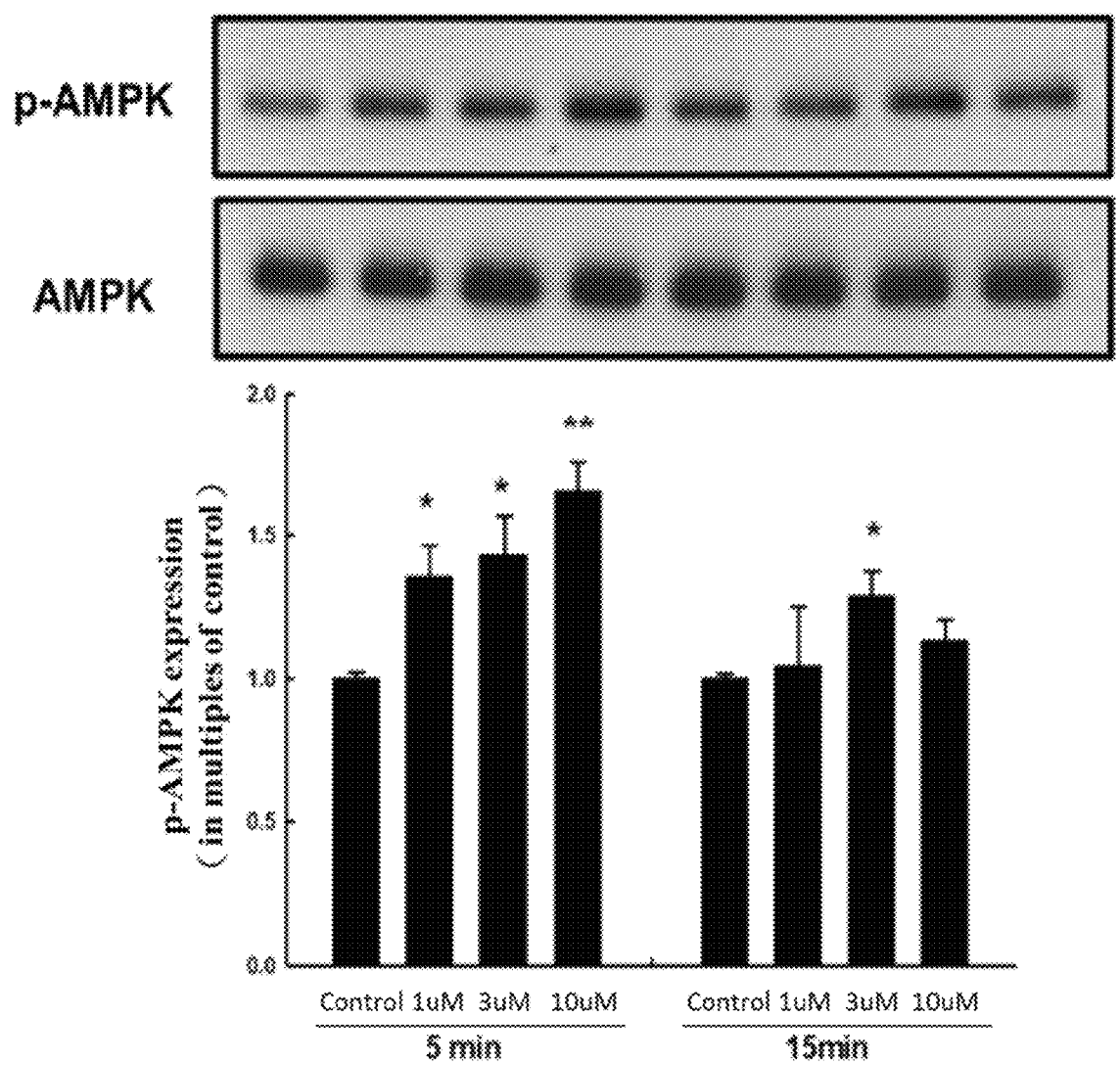
FIG. 1 shows the influence of salsolinol on AMPK phosphorylation, wherein AMPK activity tests were conducted in $C_2C_{12}$ cells with various concentrations (1, 3, and 10 µM) of salsolinol.

Unless defined otherwise, all technical and scientific terms used herein have the same meanings as commonly understood by one of skill in the art to which this invention belongs.

Unless clearly specified herein, meanings of the articles "a," "an," and "said" all include the plural form of "more than one." Therefore, for example, when the term "a component" is used, it includes multiple said components and equivalents known to those of common knowledge in said field.

As used herein, the term "activating" or "activation" refers to an action to make a molecule active, or to cause a molecule to function or act. In the invention, the activation means that the compound cause AMPK to function in the subject.

As used herein, the term "substituted" or "substitution" refers to where a functional group in a chemical compound is replaced by another group.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, rabbit, and the like).

The term "AMPK" as used herein is the abbreviation of AMP-dependent protein kinase, which refers to a type of protein kinase that regulates energy metabolism in cells, being the major regulatory factor in many biological processes. The signaling pathway of AMPK includes metabolism of glucose and lipids, and influences the expression of relevant genes and proteins. When AMPK is phosphorylated, its activity will increase and downstream proteins in the AMPK signaling pathway will be further regulated, and thereby metabolism in the liver, skeletal muscles, heart, lipid tissues and pancreas will be regulated. Therefore, medications effective in AMPK activation can be potentially effective in treating many diseases, such as metabolism diseases (such as diabetes), cancer, and cardiovascular diseases (such as atherosclerosis and ischemic heart disease). They can also be used for anti-inflammation or promoting wound healing. The mode of action of AMPK activators including anti-inflammatory activities in vascular endothelial cells has been established in some preclinical and clinical findings; therefore, AMPK is also considered as a drug target in treating cardiovascular and metabolic diseases.

The term "alkyl group" used herein refers to linear or branched monovalent hydrocarbons containing 1-20 carbon atoms, such as alkyl groups with 1-10 carbons, preferably alkyl groups with 1-6 carbons, more preferably alkyl groups with 1-3 carbons. Examples of alkyl groups include, but not limited to, methyl, ethyl, n-propyl, isopropyl, n-butyl, isobutyl, and t-butyl.

As evidenced in the examples, reticuline has an excellent effect in AMPK activation. Accordingly, the present invention provides a method for activating the AMP-dependent protein kinase (AMPK).

According to the invention, the active compound has the general Formula I:

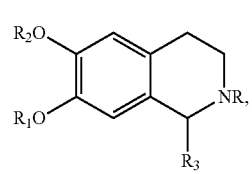

Formula I wherein R, $R_1$ and $R_2$ are each independently H, alkyl or acyl ($R_a$CO) group; $R_3$ is alkyl or substituted benzyl group; wherein $R_a$ is H or alkyl group.

In a particular example of the present invention, said substituted benzyl group has the following Formula II:

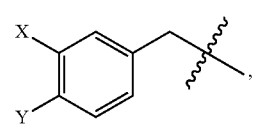

Formula II wherein X and Y are each independently H, OH, methoxy (OMe) or acyloxy ($R_b$CO—O—) group; wherein $R_b$ is H or alkyl group.

An embodiment of the active compound of the present invention is the compound having the general Formula I, wherein R=$R_1$=$R_2$=H and $R_3$=Me (methyl), which compound is salsolinol having the following formula:

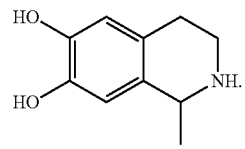

Another embodiment of the active compound of the present invention is the compound having the general Formula I, wherein R=$R_2$=Me (methyl), $R_1$=H, and $R_3$ is a substituted benzyl group of Formula II), in which X=OH and Y=OMe, which compound is reticuline having the following formula:

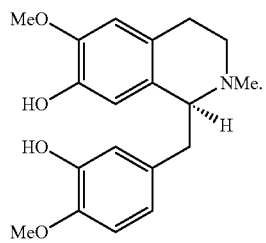

As shown in the examples of the present invention, the compound having Formula I of the present invention, such as salsolinol and reticuline, has an effect of activating AMPK and have been further verified to have an effect of reducing blood glucose, and thus can be used to treat diabetes.

Therefore, the present invention also provides a method for reducing blood glucose in a subject. Preferably, the compound having the general Formula I is salsolinol or reticuline.

In addition, the compounds having Formula I of the present invention are effective in AMPK activation so as to achieve the effect of treatment, and thus are useful in treating AMPK-dependent diseases. For examples, AMPK-dependent disease is selected from the group consisting of cancer, cardiovascular diseases, and metabolism diseases. In addition, it is also considered to have an effect in anti-inflammation or promoting wound healing.

According to the present invention, said compound having Formula I can be formulated into any forms of medications that are well known or commonly used in the pharmaceutical field, and can be prepared into a composition, according to any techniques well known in the pharmaceutical field, comprising a therapeutically effective amount of said compound in combination with a commonly used carrier or a pharmaceutically acceptable carrier.

The term "carrier" or "pharmaceutically acceptable carrier" used herein includes, but not limited to, pharmaceutically acceptable excipients, fillers, diluents, or the like, including those well known to one of ordinary skills in the pharmaceutical field.

The present invention is explained in the above description of the invention and the following examples, which should not be used to restrict the scope of the present invention.

Example 1

Preparation of the Compound Having Formula I of the Present Invention

Dopamine (1.6 g), 10 mL methanol, 1 mL 1N hydrochloric acid, and 2 mL 99% acetaldehyde were added sequentially into a 50 mL round-bottom flask and stirred for 6 hours under room temperature. The concentrate obtained by reduced-pressure concentration was loaded into a Lobar RP-18 column (size B, Merck), eluted by a 0.05% formic acid aqueous solution, to give $^1$H NMR essential pure salsolinol (1.0 g).

Based on the spectroscopic analysis, the $^1$H and $^{13}$C NMR spectroscopic data and ESIMS data of salsolinol are as follows:

$^1$H NMR (CD$_3$OD, 400 MHz) δ 6.63 (1H, s), 6.57 (1H, s), 4.30 (1H, q, J=6.8 Hz, H-1), 3.40 (1H, dt, J=12.6, 5.6 Hz, H$_a$-3), 3.20 (1H, ddd, J=12.6, 8.2, 5.6 Hz, H$_b$-3), 2.92 (1H, ddd, J=16.8, 8.2, 5.8 Hz, H$_a$-4), 2.80 (1H, dt, J=16.8, 5.6 Hz, H$_b$-4), 1.55 (3H, d, J=6.8 Hz, Me-1); ESIMS: m/z 180 ([M+H]$^+$).

Reticuline can be isolated from the wooden part of Konishi's Newlitse (*Neolitsea konishii* (H.) K. & S.), a plant of the Lauraceae family, according to known methods (*J. Chin. Chem. Soc. Taip.* 1992, 39, 189-194).

Example 2

Evaluation of the Effect of Salsolinol and Reticuline in AMPK Activation

C$_2$C$_{12}$ skeletal myoblast cell line was purchased from the Food Industry Research and Development Institute (Hsinchu, Taiwan). The C$_2$C$_{12}$ cell line was a cell line obtained from culturing the leg skeletal muscle of adult C3H mice in a cell incubator under 95% O$_2$, 5% CO$_2$, and 37° C. The cells were cultured in a DMEM medium (Gibco/Invitrogen, Carlsbad, Calif.) containing 4.5 mg/mL glucose, 10% fetal bovine serum (FBS; Gibco/Invitrogen, Carlsbad, Calif.), and an antibiotic solution (with final concentrations of penicillin=100 IU/mL and streptomycin=100 μg/mL). When the C$_2$C$_{12}$ myoblast cells have proliferated to cover seven-tenths of the area in the petri dish, the fetal bovine serum was replaced by 2% horse serum (Gibco/Invitrogen, Carlsbad, Calif.) so as to induce the C$_2$C$_{12}$ myoblast cells to become the multi-nuclei myocytes. The C$_2$C$_{12}$ myoblast cells differentiated into myocytes in 4 days, and the culture medium of the cells was replaced with no-serum DMEM 24 hours before the experiments so as to reduce metabolism of the cells.

The C$_2$C$_{12}$ myocytes were treated respectively with 1 μM, 3 μM and 10 μM salsolinol and reticuline for 5 and 15 minutes. Then the C$_2$C$_{12}$ myocytes were rinsed with PBS buffer solution, and RIPA buffer solution containing protease inhibitors (20 mM Tris-HCl (pH 7.4), 100 mM NaCl, 1 mM EDTA, 1 mM EGTA, 0.1% SDS, 0.5% sodium deoxycholate, 1% NP-40, and 100× protease inhibitor cocktail) was added into the cells. The cells were collected and centrifuged on ice. Then, the concentrations of the supernatant samples were adjusted to be the same.

The supernatant samples were put through vertical electrophoresis isolation with 8% SDS-PAGE, and the isolated proteins were transferred onto a PVDF blotting membrane. After blotting was completed, the PVDF blotting membrane was removed and blocked for 1 hour under room temperature with a blocking buffer of TBST (Tris-buffered saline with Tween-20) with 5% non-fat milk. Then, the PVDF blotting membrane was placed into a 5% BSA and TBST solution containing the primary monoclonal antibodies Phospho-AMPKα (Thr172) (Cell Signaling) (1:1000) and AMPKα (Thr172) (Cell Signaling) (1:1000), respectively, and the primary immunoblotting reaction was performed under 4° C. Then, the PVDF blotting membrane was rinsed 3 times with TBST, and a TBST solution containing the secondary antibody goat anti-rabbit IgG (Perkin Elmer) (1:10000) was added to perform the secondary reaction for one hour under room temperature. Finally, the membrane was rinsed 3 times with TBST before ECL (enhanced chemiluminescence) was added to present color.

Results

As shown in FIG. 1, after the C$_2$C$_{12}$ cells were treated with 10 μM salsolinol for 5 minutes, the AMPK phosphorylation in these cells increased to 1.66 times of that in the control cells. This shows that salsolinol has an excellent effect in AMPK activation.

Figure 2:
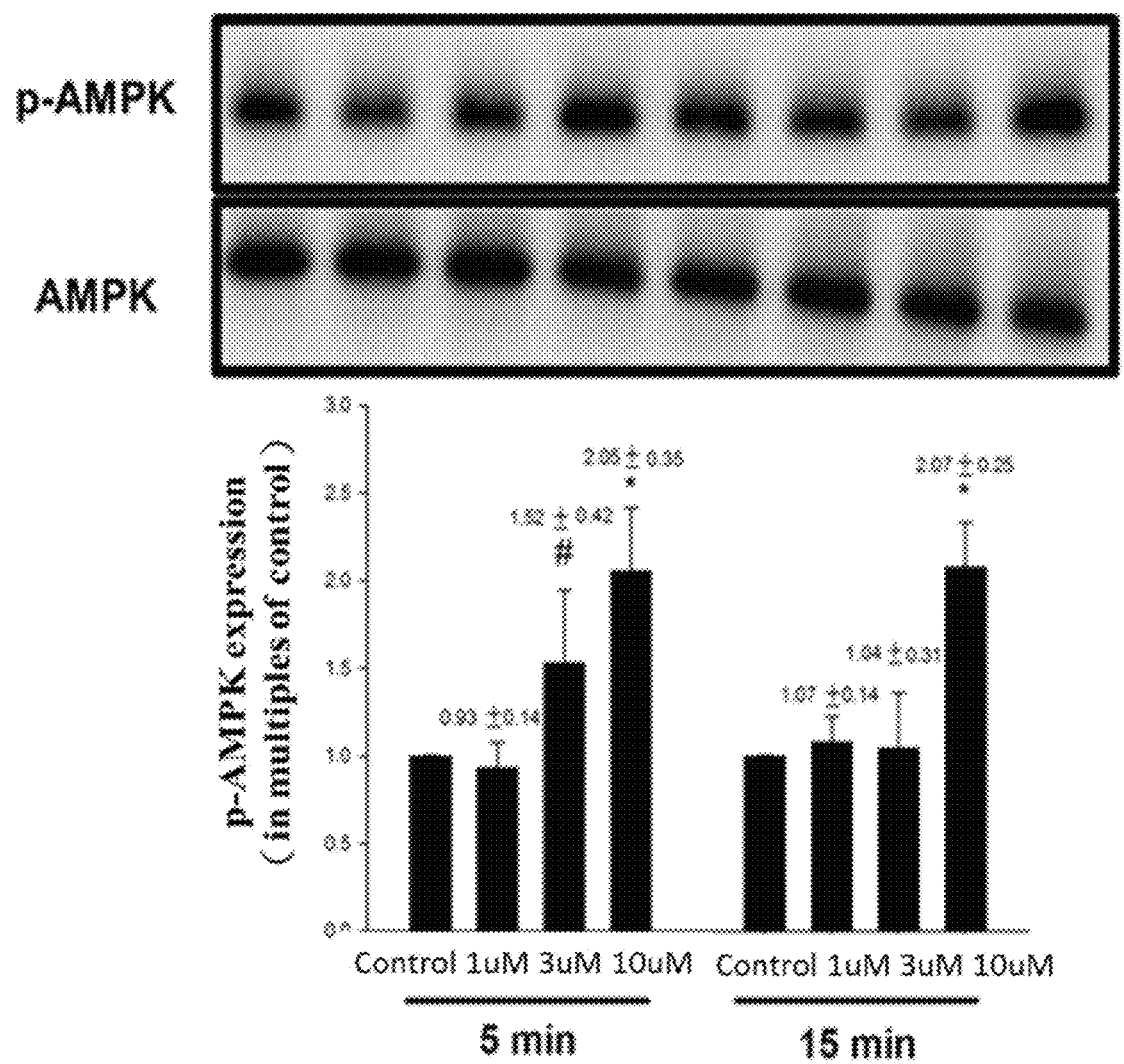
FIG. 2 shows the influence of reticuline on AMPK phosphorylation, wherein AMPK activity tests were conducted in $C_2C_{12}$ cells with various concentrations (1, 3, and 10 µM) of reticuline.

In addition, as shown in FIG. 2, after the C$_2$C$_{12}$ cells were treated with 3 μM and 10 μM reticuline for 5 minutes, the AMPK phosphorylation in these cells increased to 1.52 and 2.05 times of that in the control cells, respectively. After the C$_2$C$_{12}$ cells were treated for 15 minutes, the AMPK phosphorylation in the cells increased to 1.04 and 2.07 times of that in the control cells. These show that reticuline has an excellent effect in AMPK activation.

Example 3

Evaluation of the Effect of Salsolinol in Blood Glucose Reduction

The effect of blood glucose reduction was evaluated with the oral glucose tolerance test (OGTT). ICR mice were each fed with high-lipid food and high fructose syrup for 2 weeks, and then administered with salsolinol (10 mg/Kg/day) and Glibenclamide (10 mg/Kg) for 14 consecutive days. The mice were divided into groups of 8 for animal experiments. After administration on day 1 and the following 14 consecutive days, the mice were individually anesthetized and given salsolinol (10 mg/Kg/day) and Glibenclamide (10 mg/Kg) respectively. After 30 minutes, glucose (1 g/Kg) was orally administered and blood was taken from the mice immediately thereafter (this time point was designated as 0 minute). Blood was also taken later at 30, 60, 90, 120 and 150 minutes, and the blood glucose levels in the serum were determined after centrifugation.

Results

Figure 3:
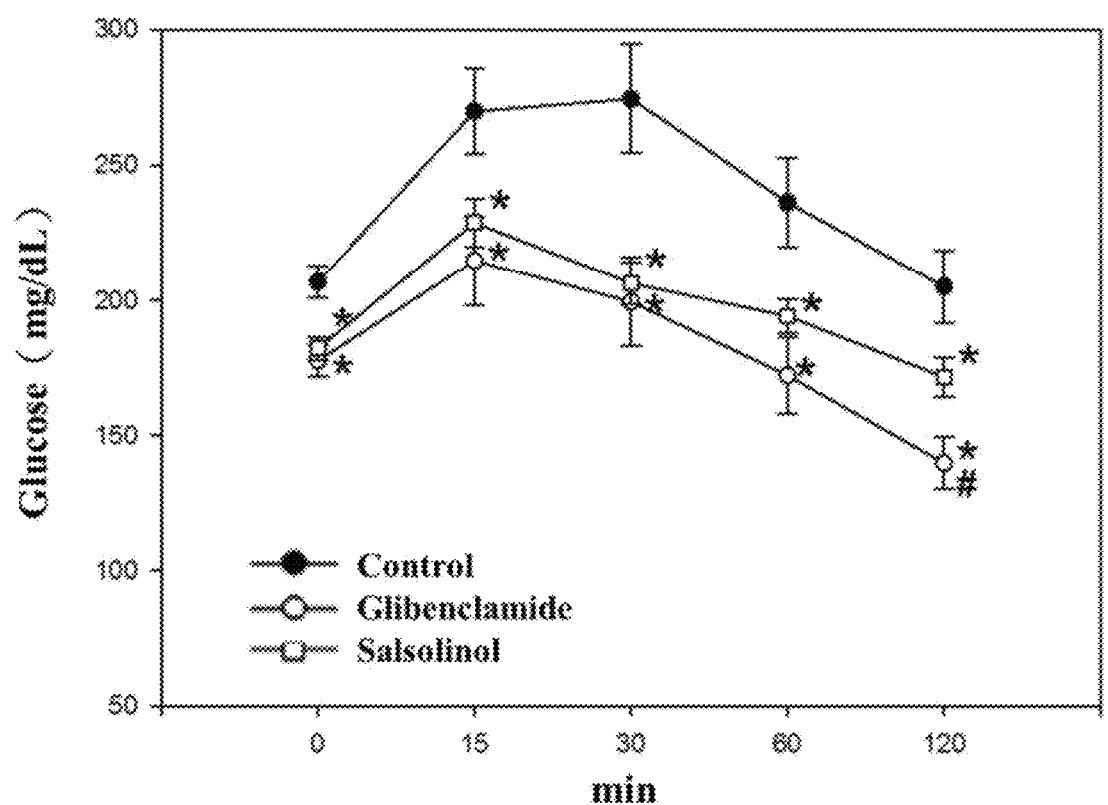
FIG. 3 shows the influence of salsolinol on the fast reduction of blood glucose. ICR mice were each fed with high-lipid food and high fructose syrup for 2 weeks. Then, salsolinol (10 mg/Kg/day) and Glibenclamide (10 mg/Kg) were administered on day 1. After 30 minutes, glucose (1 g/Kg) was orally administered and blood was taken from the mice immediately thereafter (this time point was designated as 0 minute). Blood was also taken later at 30, 60, 90, 120 and 150 minutes, and the blood glucose levels in the serum were determined.
Figure 4:
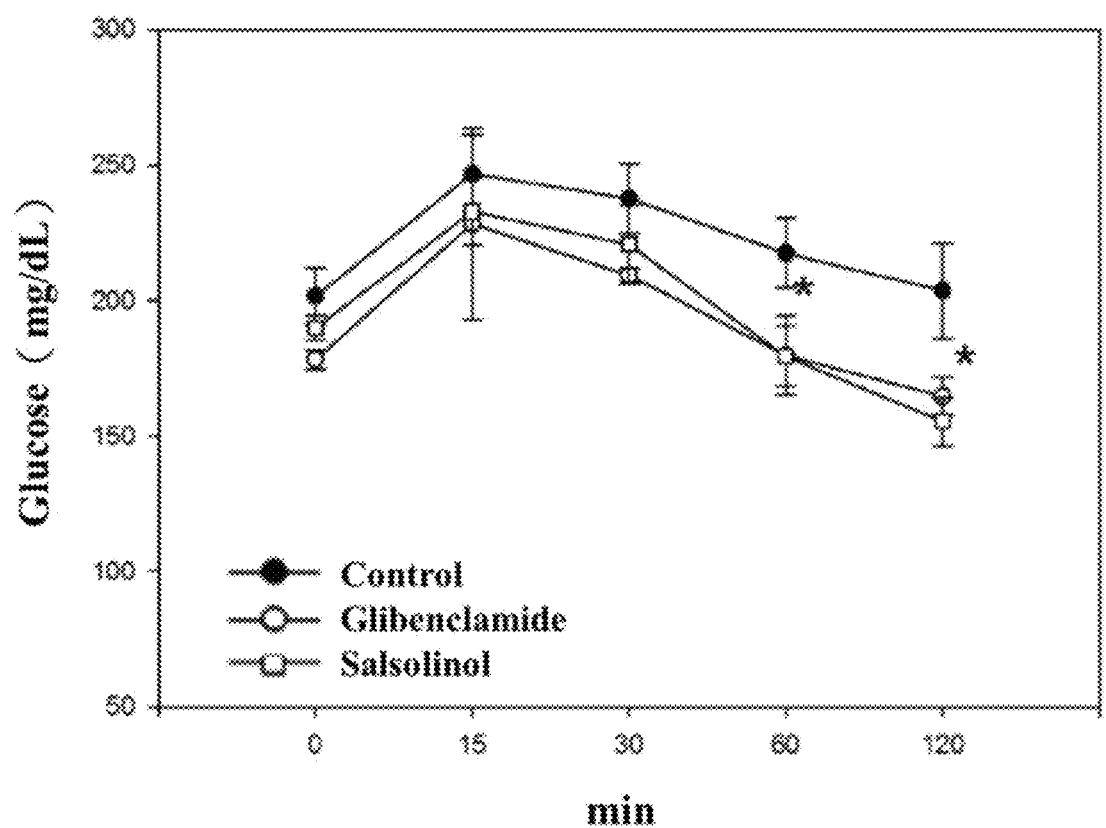
FIG. 4 shows the influence of salsolinol on the long-term reduction of blood glucose. ICR mice were each fed with high-lipid food and high fructose syrup for 2 weeks, and then administered with salsolinol (10 mg/Kg/day) and Glibenclamide (10 mg/Kg) for 14 consecutive days. Afterwards, salsolinol (10 mg/Kg/day) and Glibenclamide (10 mg/Kg) were again administered, and glucose (1 g/Kg) was orally administered after 30 minutes and blood was taken from the mice immediately thereafter (this time point was designated as 0 minute). Blood was also taken later at 30, 60, 90, 120 and 150 minutes, and the blood glucose levels in the serum were determined.

As shown in FIG. 3, in mice with Type II diabetes induced by feeding them with high-sugar high-lipid food, salsolinol has a blood glucose-reduction effect similar to that of Glibenclamide in terms of the fast reduction of blood glucose. As shown in FIG. 4, it was further found that salsolinol also has a blood glucose-reduction effect similar to that of Glibenclamide in terms of the long-term reduction of blood glucose.

Based on the results in the examples, one can see that salsolinol has an excellent effect in AMPK activation. In addition, salsolinol has a blood glucose-reduction effect similar to that of Glibenclamide. However, Glibenclamide also affects the secretion of insulin, while as opposed to Glibenclamide, salsolinol has a lower effect on insulin secretion. Reticuline also has an excellent effect in AMPK activation. Even 10 µM reticuline can provide a pretty good effect.

We claim:

1. A method for reducing blood glucose comprising administering to a subject in need thereof a pharmaceutical composition comprising a pharmaceutically acceptable carrier and a therapeutically effective amount of salsolinol or reticuline.

2. A method for treating diabetes comprising administering to a subject in need thereof a pharmaceutical composition comprising a pharmaceutically acceptable carrier and a therapeutically effective amount of salsolinol or reticuline.

* * * * *